(12) United States Patent
Fischer et al.

(10) Patent No.: US 7,976,860 B2
(45) Date of Patent: Jul. 12, 2011

(54) IMPLANT AND PROCESS FOR ITS PRODUCTION

(75) Inventors: Heike Fischer, Meerbusch (DE); Monika Schulze, Hechingen (DE)

(73) Assignee: JOTEC GmbH, Hechingen (DK)

( * ) Notice: Subject to any disclaimer, the term of this patent is extended or adjusted under 35 U.S.C. 154(b) by 222 days.

(21) Appl. No.: 11/849,631

(22) Filed: Sep. 4, 2007

(65) Prior Publication Data

US 2008/0057126 A1 Mar. 6, 2008

(30) Foreign Application Priority Data

Sep. 5, 2006 (DE) .......................... 10 2006 042 631

(51) Int. Cl.
*A61K 31/19* (2006.01)
*A61K 31/727* (2006.01)
*A61K 38/00* (2006.01)
*A61K 9/14* (2006.01)
*A61P 43/00* (2006.01)

(52) U.S. Cl. .............. 424/423; 424/484; 514/2; 514/56; 514/568

(58) Field of Classification Search ........................ None
See application file for complete search history.

(56) References Cited

U.S. PATENT DOCUMENTS

| | | | |
|---|---|---|---|
| 4,787,900 A | 11/1988 | Yannas | |
| 2001/0053933 A1* | 12/2001 | Phaneuf et al. | 623/1.48 |
| 2002/0177903 A1* | 11/2002 | Geistlich et al. | 623/23.72 |
| 2003/0023318 A1* | 1/2003 | Simmoteit et al. | 623/23.76 |

FOREIGN PATENT DOCUMENTS

| | | |
|---|---|---|
| EP | 0 562 864 A1 | 9/1993 |
| WO | WO 99/27315 | 6/1999 |

OTHER PUBLICATIONS

Patino et al. "Collagen as an Implantable Material in Medicine and Dentistry" Journal of Oral Implantology: vol. 28, No. 5,pp. 220-225.*

* cited by examiner

*Primary Examiner* — Robert A Wax
*Assistant Examiner* — Danah Al-Awadi
(74) *Attorney, Agent, or Firm* — Harness, Dickey & Pierce, P.L.C.

(57) ABSTRACT

The present invention relates to an implant having a structured material component and having a protein matrix which has a pore structure. The structured material component is moreover at least partly anchored in the protein matrix. The implant also has on at least one its surfaces a protein membrane crosslinked with the protein matrix.

18 Claims, 1 Drawing Sheet

IMPLANT AND PROCESS FOR ITS PRODUCTION

CROSS-REFERENCES TO RELATED APPLICATIONS

This application claims priority from German patent application DE 10 2006 042 631.2, filed on Sep. 5, 2006.

BACKGROUND OF THE INVENTION

The invention relates to an implant, in particular a vascular prosthesis which has a structured material component and a protein matrix with pore structure, and to process for its production and its use.

Many implants and processes for their production are known in the art. "Implants" generally mean devices which are inserted into a patient's body, at least temporarily, and which are intended to exert for example therapeutic, supporting or articular functions.

Implantable structures are used especially in the field of tissue engineering, an interdisciplinary research area which is concerned with processes and materials for producing artificial tissue and organ systems. Thus, for example, artificially produced implants can be used as skin, bone, cartilage, lens or vessel substitute.

Implants in the form of vascular prostheses are employed as substitute for a natural diseased vessel. The diseased section of vessel is removed and replaced by an implant. Thus, for example, small-lumen implants are employed in vascular surgery especially when the endogenous vessels of a patient cannot be used. This is the case for example when a specific length of vessel is required, or if the autologous vessels cannot be employed because of pathophysiological properties. Vascular prostheses made of synthetic material are employed here, use being made in particular of synthetic materials such as, for example, knitted or woven threads of polyethylene terephthalate (PET) or vascular prostheses made of expanded polytetrafluoroethylene (ePTFE).

Vascular implants made of these synthetic materials are preferably used because they have advantageous structural and biocompatible properties. Thus, on the one hand, surrounding tissue is able to grow in and, on the other hand, blood plasma must not escape through the pores. This is achieved through the pore size adjusted with the ePET implants, whereas knitted and woven PET implants are impregnated by coating with absorbable materials such as, for example, collagen or gelatin. Following implantation, the coating is absorbed at the rate at which the surrounding newly formed tissue grows into the porous collagen layer.

It is known that the use of the implants described above in the small-lumen vessel range leads to high rates of occlusion. This is because in particular contact of slow-flowing blood with synthetic surfaces may lead to activation of the coagulation system, the complement system and the immune system.

Further approaches to avoiding blood coagulation are in the direction of colonizing the coated implants with cells such as, for example, endothelial cells and smooth muscle cells. Interaction of the various cell types which are present for example in natural vessels, and the cell-matrix interaction are important for the functionality of the implants. Thus, besides high biocompatibility, it is also necessary to ensure that the structure of the implant is suited to the requirements of various cells.

Implants are subject to special mechanical and structural requirements. Thus, besides a sufficient structural stability, they should also have a force and stretching behaviour adapted to the tissue to be replaced. Implants must additionally have various fitting shapes, lengths and diameters. In addition, the microstructuring such as, for example, in the bioartificial vessel substitute the pore structure extending radially with cell-specific size plays an important role for the colonization with cells and for the growing tissue.

RELATED PRIOR ART

To provide a suitable pore structure, in the prior art inter alia sponges, or implants including a sponge, are provided. Thus, for example, WO 99/27315 discloses a process for producing porous structures in which a liquid or pasty mixture is solidified by cooling from two sides. A homogeneous porous structure can be produced in this way.

EP 0 562 864 further discloses heteromorphic sponges which include active ingredients. The heteromorphic sponges additionally include at least one substructure which, like the matrix structure of the sponge, are produced from absorbable biopolymeric materials. It is evident from the description of this patent application that in the production of the heteromorphic sponges firstly an appropriate sponge is produced by freezing, and subsequently a collagen film is placed on the frozen sponge, a further layer of collagen suspension is applied over the collagen film, and this composite is subsequently freeze-dried.

However, this implant is disadvantageous in that an aligned pore structure of the sponge cannot be achieved, the reason for this being that blast freezing is employed. In addition, the collagen film is not anchored in the sponge-like structure by placing on the collagen sheet and further application of a collagen suspension and freezing thereof.

However, anchoring of the various layers is desired in order to confer adequate stability and elasticity on the implant in order to be able to manipulate the implant with appropriate flexibility.

DE 101 35 275 discloses an implant and a process for its production which includes a protein matrix with a directed pore structure, where the protein matrix is anchored in a further layer (foreign structure). The implant disclosed in DE 101 35 275 has the advantage over the previously described implants that, owing to the production process, they have a directed pore structure because of which for example cells can grow in optimally.

The implant disclosed in DE 101 35 275 is disadvantageous in that the uncolonized implant is not sealed immediately after application of cells, possibly resulting during the colonization under flow in media escaping at the vessel inlet and media entering at the end of the perfused vessel. The formation of an endothelial monolayer is therefore possible only with difficulty.

Although a wide range of implants is available with the implants currently sold on the market, there is nevertheless a great need to provide further embodiments with which the properties essential for implants, such as sufficient stability with, at the same time, flexibility, are improved, which make easy manipulation possible and moreover are biocompatible and easily absorbable.

SUMMARY OF THE INVENTION

The invention is therefore based on the object of providing an implant and a process for its production with which on the one hand the disadvantages of the implants disclosed in the prior art can be overcome, and which is able to comply with the advantages just described.

With the implant mentioned at the outset, the object is achieved according to the invention by an implant in which the structured material component is at least partly anchored in the protein matrix, and in which the implant has a protein membrane on at least one surface.

The object is further achieved by a process for producing an implant which has the structure according to the invention.

The object underlying the invention is thus completely achieved.

The protein membrane provided on the implant provides a surface suitable for colonization by cells, for example endothelial cells, and for rapid formation of a cell monolayer. The protein membrane is configured in such a way that it is liquid-impermeable without representing a diffusion barrier, and is thus impervious for escape and entry of flow.

In the case where the implant is configured as vascular implant, the protein membrane forms the inner side of the vessel, whereby this inner side of the vessel is colonized by endothelial cells to form an endothelial monolayer.

In the case where the implant is configured as tissue implant, the protein membrane is disposed on the surface as delimiting layer.

In this connection, "structured material component" means any continuous or coherent structure which has a layered configuration and forms a type of framework for the implant which is either entirely contained in the protein matrix or else serves as boundary layer into which the protein matrix can be partly introduced. "Structured" means in this connection that the material component has pores or undercuts by which the material component can be anchored in the protein matrix.

It is possible by the implant according to the invention to provide for the first time vascular and/or tissue implants which have adequate stability, which depending on the choice of structured material component—are absorbed completely or virtually completely, and which are suited by their micro-structuring to the specific requirements of cells during the application of cells, the culturing and the formation of new tissue. Thus, the protein membrane forms a suitable basis for the adhesion of cells and the formation of a cell monolayer, such as, for example, the formation of an endothelial monolayer in the case of a bioartificial vascular implant. The protein matrix with an open pore structure which extends in directed fashion (i.e. in a single direction) and has a suitable pore size makes uniform cell distribution within the matrix possible during the colonization. The cells are embedded in a protein matrix similar to the natural situation. In the bioartificial vessel substitute, the pore structure is suited for example to the requirements of smooth muscle cells.

In one embodiment, the structured material component is completely anchored in the protein matrix.

In this embodiment, the pores present in the protein matrix grow through the structured material component, so that the structured material component is completely surrounded by the protein matrix, or is taken up in the protein matrix. The pores or meshes of the structured material component are many times the size of those in the protein matrix and thus do not form a cell barrier. At the same time, adequate stability is conferred on the sponge-like structure of the protein matrix by the structured material component incorporated into the protein matrix. In addition, the protein membrane applied to the surface at the same time provides a liquid-impermeable structure as boundary to the surroundings, that is to say creates a type of seal which serves as barrier to escape of blood for example when the implant is elaborated as vascular implant.

The introduction of the protein membrane makes the implant already liquid-impermeable when cells are applied. It is thus possible advantageously to carry out the colonization at defined shear rates. The colonization time until a cell monolayer forms can thus be advantageously reduced.

In a further embodiment, the structured material component is only partly incorporated into the protein matrix, and the structured material component forms an outer boundary layer of the implant.

This embodiment of the implant thus has a layered structure, with the layer of the protein matrix being introduced between on the one hand the structured material component in which it is partly anchored, and the protein membrane on the other hand.

The structured material component can in this connection include any material which forms or specifies a structured shape. Suitable examples of structured material component are therefore structured resistant synthetic materials, structured absorbable synthetic materials, structured natural materials, and mixtures of said materials.

The structured material component may include a material which is selected from the group comprising polytetrafluoroethylene, polyurethane, polystyrene, polyester, ceramic, metal, polylactitol, polyglycolic acid, polyhydroxyalkanoates, copolymers thereof, polysaccharides or mixtures of one or more of said materials.

In a further embodiment, the structured material component includes polyester which, in the case of a vascular prosthesis, can be configured as a wide-mesh net-like tube. Nevertheless, other materials are also conceivable as tube-like basic frameworks of the foreign structure, for example expanded polytetrafluoroethylene, which has become widely used recently as preferred synthetic material for implants.

In a refinement, the protein membrane includes a material which is selected from the group comprising collagen, elastin, cellulose, chitosan, chitin and components of the extracellular matrix or a mixture of two or more of these substances.

The protein membrane can moreover have a layer thickness of between 0.02 mm and 5 mm.

It is further preferred with the implant of the invention for the protein matrix to have a pore size of about 5 μm to 500 μm.

It is further preferred for the protein matrix into which the structured material component is introduced to have a layer thickness of about 0.05 mm to about 50 mm.

In a refinement, the implant is configured as a tubular vascular prosthesis/vascular implant, wherein the protein membrane may be formed in the inner side of the tubular vascular prosthesis.

Accordingly, this embodiment provides a vascular prosthesis which, because of its configuration, on the one hand ensures regeneration of the vessel wall, neovascularization from the surrounding tissue and good nutrient supply in the protein matrix, and which on the other hand, because of the inner lining with the protein membrane, prevents blood escaping into the surrounding tissue. At the same time, the protein membrane provides a layer for colonization by endothelial cells, upon which an endothelial monolayer can easily be formed.

In further refinements, the implant additionally includes at least one active ingredient which is selected from the group comprising heparin, hirudin, aspirin, heparan sulphate, albumin, antibiotics such as, for example, rifampicin, and/or growth factors.

Depending on the application, the implants can be loaded or coated with active ingredients before implantation. It is possible in this connection for the active ingredient delivery subsequently to be additionally controlled for example by an additionally applied hydrogel coating or by the nature of the binding of the active ingredients.

A further refinement in this connection is where the protein membrane is crosslinked with the protein matrix without crosslinker.

This is achieved for example by crosslinking the protein membrane with the protein matrix by a cooling step during the production of the implant.

In another refinement, the crosslinking of the protein membrane with the protein matrix (or a further/additional crosslinking) is achieved by chemical crosslinkers (such as, for example, glutaraldehyde).

The invention further relates to a process for producing the implants of the invention, which includes the following steps:
a) provision of a protein membrane on a first delimiting shape corresponding to the basic shape of the protein membrane in an arrangement;
b) positioning of the structured material component over the protein membrane in the arrangement, where the shape of the foreign structure corresponds to the basic shape of the protein membrane;
c) application of a second delimiting shape to the structured material component;
d) introduction of a suspension between protein membrane and structured material component, and
e) cooling of the arrangement and subsequent freeze-drying to form a protein matrix from the suspension and to bind on the protein membrane.

Thus, in this process, firstly a prefabricated protein membrane is applied to a first shape—corresponding to the shape of the prefabricated protein membrane—this shape forming a first delimitation for the implant construct during the production of the implant. The shape can serve where appropriate during a one-sided freezing process as cooling plate or insulation. Subsequently, a structured material component is positioned over the protein membrane, with a second delimiting shape which can, where appropriate depending on the arrangement, serve as cooling plate or for insulation being applied to the structured material component. In a next step, a suspension is introduced between the protein membrane and the structured material component, and the complete arrangement is cooled and freeze-dried. Before the freeze-drying, one of the boundary shapes is removed in order to expedite the freeze-drying step. The cooling results in the formation of a protein matrix from the suspension, with at the same time this protein matrix being on the one hand partly anchored in the structured material component, and on the other hand crosslinked with the protein membrane, during this step.

Depending on the distance of the second delimiting shape from the foreign structure it is possible for example for the pores resulting in the protein matrix for example to grow through the structured material component. It is possible in this case for example for the protein matrix which has grown through the structured material component to be, after completion of the implant, cut off or shortened appropriate for the purpose of use. On the other hand, it is also possible, by putting the delimiting second shape in direct contact, for the pores not to grow completely through the structured material component but merely be anchored in the structured material component.

In one embodiment of the process of the invention, the cooling in step e) takes place one-sidedly. The one-sided cooling can result in formation of a directed pore structure, making it possible for cells to be embedded uniformly during the colonization. In this process, the arrangement is one-sidedly cooled on one side or surface, while the other surface is insulated. The suspension may crystallize partly or completely during the freezing process.

Implants produced by the preferred process may for example—on use of a metal tube as basic shape—represent vascular implants, although it is also possible to produce flat tissue implants by using appropriately flat basic shapes.

In the abovementioned embodiment of the process of the invention, the cooling in step e) proceeds at a constant cooling rate and in particular at a cooling rate of about 0.1 K/min to 200 K/min.

It is possible by using different cooling rates to adjust different pore sizes of the protein matrix. In this connection, faster cooling results in a smaller pore size. It is possible for example with a cooling rate of 12 K/min to adjust a pore size of about 45 µm to 50 µm, and a pore size of about 85 µm to 105 µm with a cooling rate of 1 K/min, it being possible to influence the respective ranges for example by adding acids such as acetic or ascorbic acid.

The use of one-sided cooling has proved to be particularly suitable for producing the implant of the invention because directed pores can be produced in this way.

In a refinement of the process of the invention, the cooling in step e) takes place at a constant temperature.

In this variant, the arrangement can for example be cooled in a freezer or other suitable cooling or freezing devices. However, these implants then do not have a directed pore structure but are likewise suitable—depending on the application—for use as implants.

It is further preferred in the process of the invention for the suspension from which the protein matrix is formed to be a suspension which comprises collagen, elastin and soluble, non-collagenous constituents.

Additional concomitant substances may be growth factors or constituents of the extracellular matrix such as, for example, laminin, elastin, fibronectin, hyaluronic acid, glycosaminoglycans inter alia, and derivatives thereof. The soluble constituents include on the one hand acids such as HCl, acetic acid or ascorbic acid, because it is known that the optimal pH range for producing freeze-dried collagen sponges is between 2.5 and 3.5. It is possible on the other hand to employ soluble additives such as glycerol or ethanol or finely dispersed substances such as, for example, calcium phosphate, because the morphology of ice crystals and thus the pore structure can be adjusted through their concentration.

A further embodiment provides for the protein membrane employed in step a) to be produced from the same suspension as the suspension for producing the protein matrix and—depending on the use of the implant—to be configured in planar or tubular shape.

In the case of the one-sided freezing process, during which the suspension may crystallize, the collagens, elastin and the dissolved substances are displaced by the growing cellular one-phase front, with the suspended proteins and the dissolved or dispersed substances being highly concentrated between the ice crystals. It is possible advantageously to adjust the ice crystal structure and size for any layer thickness by the cooling rate and the chemical composition of the protein suspension.

In a refinement of the process of the invention there is provision of a further step f) with which the implant produced in steps a) to e) is subsequently freeze-dried.

During the freeze-drying process, the ice crystals sublime, resulting in pores which correspond to the single-crystal morphology of the frozen sample. On colonization of the protein matrix it is possible for cells to be distributed uniformly in the pores. It is furthermore possible on implantation for the cells of the surrounding tissue to grow into the implant along the protein fibres. Through the removal of water during the sublimation, covalent bonds form between the collagen molecules, whereby the matrix, the membrane and the matrix-membrane connection acquire the desired stability. It is advantageous in this connection that targeted adjustment of the degree of crosslinking is possible through the freeze-drying process or through a chemical treatment of the freeze-dried product. The protein matrix resulting from the freeze-drying process is thus directly anchored to the membrane and the foreign structure, and no further steps are necessary for connecting the foreign structure and the membrane to the protein matrix.

It is possible by the invention to achieve with simple means the possibility of simple and efficient adaptation of the implant to the respective requirements of the surrounding tissue through the formation of a pore structure and the binding on of a membrane. The implants produced in this way exhibit mechanical stability and biological compatibility.

The invention further relates to implants produced by the process of the invention, and in particular to vascular prostheses/vascular implants. Such vascular prostheses can be employed for example as small-lumen vessel substitute (diameter <6 mm), e.g. for coronary vessels or peripheral vessels, and as dialysis shunt or in pediatrics as concomitantly growing vascular implants.

Further advantages are evident from the description and the appended drawings.

It will be appreciated that the features mentioned above and to be explained below can be used not only in the combination indicated in each case, but also in other combinations or alone, without departing from the scope of the present invention.

BRIEF DESCRIPTION OF THE DRAWINGS

Exemplary embodiments of the invention are depicted in the following drawings and are explained in detail in the following description. These show.

Figure 1:
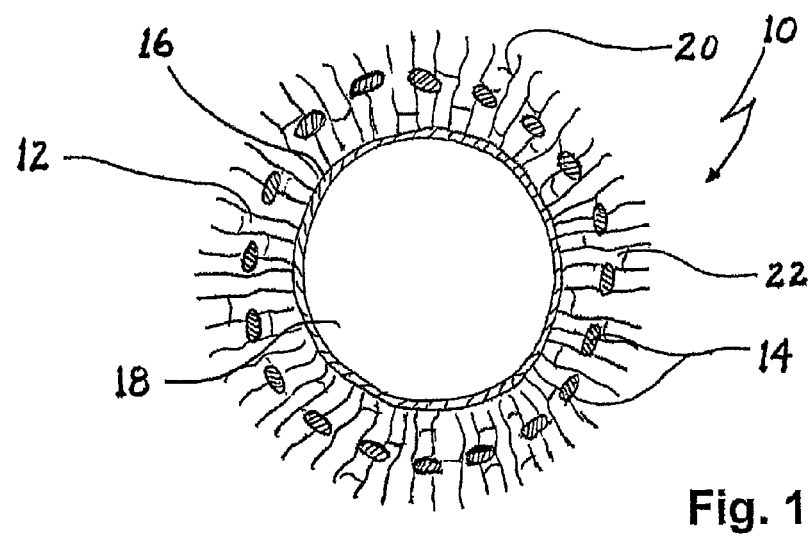
FIG. 1 a cross section of an exemplary embodiment of an implant of the invention, specifically a vascular prosthesis.

DETAILED DESCRIPTION OF PREFERRED EMBODIMENTS 10 in FIG. 1 designates overall a vascular implant 10 which has been produced by the process of the invention. A protein matrix 12 is deeply anchored in a structured material component 14 in the implant. The inner wall of the vascular implant 10 is formed by a protein membrane 16 which represents the boundary to the lumen 18. The protein matrix 12 consists of protein fibres 20 with pores 22.

An adequate stability and suturability is conferred on the vascular implant 10 by the structured material component 14, which is present like a framework in the protein matrix. The pores 22, which extend in directed fashion, of the protein matrix 12 can be colonized uniformly with cells such as, for example, smooth muscle cells, and in vivo it is possible for cells to grow in from the surrounding tissue. On the other hand, the inner wall, or protein membrane 16, of the vascular implant 10 can be colonized with endothelial cells because the protein membrane 16 provides a suitable surface for formation of an endothelial monolayer.

It is noted at this point that the vascular implant 10 shown in FIG. 1 represents only one exemplary embodiment. Besides this, the invention can also be employed in other shapes and functions such as, for example, as patches for skin implants, as cylinder or rectangle for cartilage and bone implants or heart valves.

It is possible by the process to produce implants with different layer thicknesses of the protein matrix. A particular temperature profile is applied in order to achieve a particular layer thickness of the protein matrix.

Figure 2:
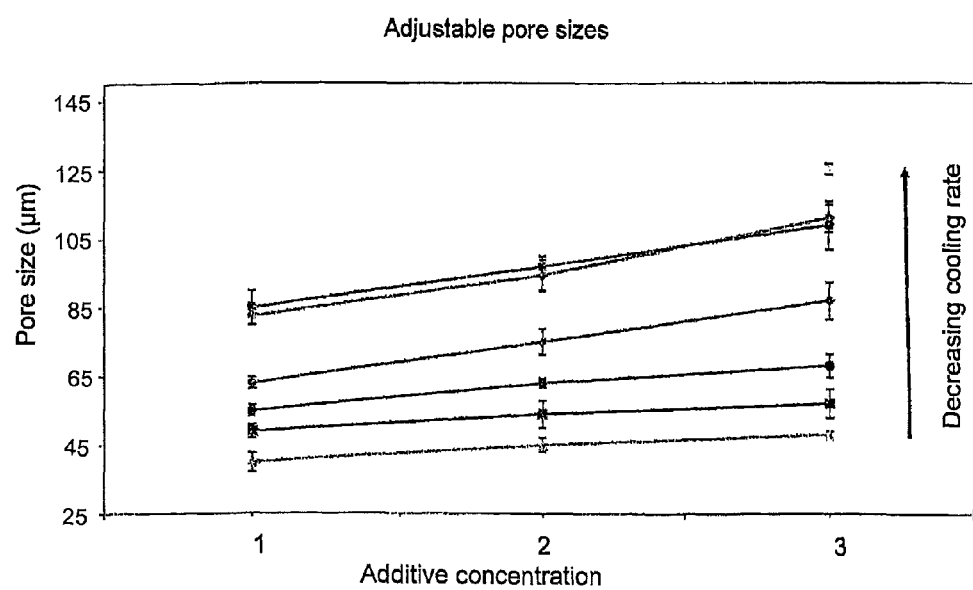
FIG. 2 a diagram which depicts the dependence of the pore size on the acetic acid concentration.

In this connection, FIG. 2 shows a diagram in which the dependence of the pore size taking account of the acetic acid concentration and the cooling rate is depicted. It is evident from the diagram that larger pores can be produced with a lower cooling rate (see, for example, 0.5 K/min compared with 12 K/min) and that, when the acetic acid concentration is simultaneously raised, the pore size was likewise larger than with a lower acetic acid concentration (see, for example, at the cooling rate of 1 K/min: 1.5% acetic acid: 85 µm pore size compared with 3.8% acetic acid: about 110 µm pore size).

The use of the device is now shown by means of the example described below.

EXAMPLE

Production of a Vascular Implant of the Invention

A wide-mesh textured polyester net was knitted, cleaned and shrunk by known processes. The polyester net in collagen suspension was completely deaerated in a desiccator.

A tubular collagen/collagen-elastin membrane with the desired internal diameter of the resulting vascular implant was produced from the collagen suspension or the collagen-elastin suspension by extrusion or by producing a flat collagen membrane and subsequent tube formation with collagen suture. This collagen/collagen-elastin membrane (protein membrane) was placed in the desired length on for example a metal tube; the polyester net (that is to say the structured material component) was pushed over the protein membrane, and a second tubular shape was applied to the structured material component which, depending on design, can serve as cooling plate or for insulation. In a next step, a (collagen/collagen-elastin) suspension was introduced between protein membrane and structured material component.

The arrangement was then cooled, i.e. the collagen/collagen-elastin suspension undergoes directed solidification—for example by a unilaterally controlled freezing step. For this purpose, the temperature of the metal tube, which now acts as cooling tube, is reduced at a constant cooling rate of, for example, 6 K/min. Ethanol serves as cooling medium and is pumped continuously through the metal tube.

After the freezing, the second shape is removed. The samples are stored at <−45° C. for at least 12 hours and then freeze-dried.

After a subsequent sterilization, the vascular prosthesis produced by the process of the invention and consisting of a collagen/collagen-elastin matrix, collagen/collagen-elastin membrane and a polyester reinforcement is ready for colonization by, for example, myofibroblasts, endothelial cells and smooth muscle cells in a cell reactor.

As already mentioned, the implant is already liquid-impermeable, owing to the introduction of the protein membrane, when cells are applied. It was possible with the implant of the invention to reduce the colonization time until a cell monolayer formed to a maximum of four days.

What is claimed is:

1. Implant having a first layer comprising a structured material component and a protein matrix which has a pore structure, wherein the structured material component is completely embedded in the protein matrix, and a second layer comprising a protein membrane crosslinked with the protein matrix, and further wherein the implant is configured as a tubular vascular prosthesis defining an interior and wherein the protein membrane comprises the interior surface of the tubular vascular prosthesis.

2. Implant according to claim 1, wherein the structured material component includes the material which is selected from the group comprising polytetrafluoroethylene, polyurethane, polystyrene, polyester, ceramic, metal, polylactide, polyglycolic acid, polyhydroxyalkanoates, copolymers thereof, polysaccharides or mixtures of one or more thereof.

3. Implant according to claim 1, wherein the protein matrix has a pore size of about 5 μm to 500 μm.

4. Implant according to claim 1, wherein the protein matrix into which the foreign structure is introduced has a layer thickness of about 0.05 mm to about 50 mm.

5. Implant according to claim 1, wherein the implant further includes an active ingredient which is selected from the group comprising heparin, hirudin, aspirin, heparan sulphate, albumin, antibiotics, growth factors, or mixtures of one or more of these active ingredients.

6. Implant according to claim 1, wherein the protein membrane is crosslinked with the protein matrix without crosslinker.

7. Implant according to claim 1, wherein the protein membrane is connected to the protein matrix by crosslinker.

8. Implant according to claim 7, wherein the crosslinker is selected from the group comprising glutaraldehyde, formaldehyde, isocyanates, ethylene dichloride, or mixtures of one or more of these crosslinkers.

9. Implant according to claim 1, wherein the protein matrix has a directed pore structure.

10. A tubular vascular implant including an outer layer comprising a protein matrix having a pore structure and a structured material component completely embedded within said protein matrix, and an inner layer comprising a protein membrane, wherein the protein membrane comprises the interior surface of the tubular vascular implant and further wherein the protein membrane is cross-linked with the protein matrix in said outer layer.

11. Implant according to claim 10, wherein the structured material component includes the material which is selected from the group comprising polytetrafluoroethylene, polyurethane, polystyrene, polyester, ceramic, metal, polylactide, polyglycolic acid, polyhydroxyalkanoates, copolymers thereof, polysaccharides or mixtures of one or more thereof.

12. Implant according to claim 10, wherein the protein matrix has a pore size of about 5 μm to 500 μm.

13. Implant according to claim 10, wherein the protein matrix into which the foreign structure is introduced has a layer thickness of about 0.05 mm to about 50 mm.

14. Implant according to claim 10, wherein the implant further includes an active ingredient which is selected from the group comprising heparin, hirudin, aspirin, heparan sulphate, albumin, antibiotics, growth factors, or mixtures of one or more of these active ingredients.

15. Implant according to claim 10, wherein the protein membrane is crosslinked with the protein matrix without crosslinker.

16. Implant according to claim 10, wherein the protein membrane is connected to the protein matrix by crosslinker.

17. Implant according to claim 16, wherein the crosslinker is selected from the group comprising glutaraldehyde, formaldehyde, isocyanates, ethylene dichloride, or mixtures of one or more of these crosslinkers.

18. Implant according to claim 10, wherein the protein matrix has a directed pore structure.

* * * * *

UNITED STATES PATENT AND TRADEMARK OFFICE
CERTIFICATE OF CORRECTION

PATENT NO. : 7,976,860 B2
APPLICATION NO. : 11/849631
DATED : July 12, 2011
INVENTOR(S) : Heike Fischer et al.

It is certified that error appears in the above-identified patent and that said Letters Patent is hereby corrected as shown below:

Title Page, Item (73) Assignee
"Hechingen (DK)" should be -- Hechingen (DE) --.

Signed and Sealed this
Twenty-second Day of November, 2011

David J. Kappos
*Director of the United States Patent and Trademark Office*